United States Patent
Bollinger et al.

[11] Patent Number: 6,100,096
[45] Date of Patent: Aug. 8, 2000

[54] NITRIC OXIDE DETECTOR

[75] Inventors: Mark J. Bollinger, Golden; John W. Birks; Jill K. Gregory, both of Boulder, all of Colo.

[73] Assignee: 2B Technologies, Inc., Golden, Colo.

[21] Appl. No.: 09/037,311

[22] Filed: Mar. 9, 1998

[51] Int. Cl.[7] .................................................. G01N 33/00
[52] U.S. Cl. .............................. 436/116; 422/81; 422/82; 422/83; 422/88; 422/91; 435/4; 436/106; 436/117; 436/118; 436/172; 436/175; 436/177; 436/178
[58] Field of Search ..................................... 436/106, 116, 436/117, 118, 172, 175, 177, 178, 181; 135/4; 422/81, 82, 82.05, 83, 88, 91

[56] References Cited

U.S. PATENT DOCUMENTS

| | | | |
|---|---|---|---|
| 3,659,100 | 4/1972 | Anderson et al. | 250/71 R |
| 3,679,312 | 7/1972 | Mansberg. | |
| 3,700,896 | 10/1972 | Anderson et al. | 250/71 R |
| 3,710,107 | 1/1973 | Warren et al. | 250/71.5 R |
| 3,797,999 | 3/1974 | Witz et al. | 422/52 X |
| 3,940,250 | 2/1976 | Plakas et al. | 23/230 B |
| 4,268,279 | 5/1981 | Shindo et al. | 55/16 |
| 4,765,961 | 8/1988 | Schiff et al. | 422/52 |
| 4,912,051 | 3/1990 | Zaromb | 436/178 |
| 4,942,135 | 7/1990 | Zaromb | 436/178 |
| 5,094,817 | 3/1992 | Aoki et al. | 436/124 X |
| 5,271,894 | 12/1993 | Kozakura et al. | 422/52 |
| 5,424,216 | 6/1995 | Nagano et al. | 436/116 |
| 5,434,085 | 7/1995 | Capomacchia et al. | 436/116 |
| 5,451,788 | 9/1995 | Pollack | 422/52 |

OTHER PUBLICATIONS

T. Fujiwara et al. Spectrochim. Acta Rev. 1990, 13, 399–406.
M. A. LaPack et al. Anal. Chem. 1991, 63, 1631–1637.
A. B. Shelekhin et al. J. Membrane Sci. 1992, 73, 73–85.
R. S. Lewis et al. Biol. Mass Spectrom. 1993, 22, 45–52.
D. P. Lucero ISA Trans. 1977, 16, 71–80.
J. R. Poulsen et al. Chromatographia 1986, 22, 231–234.
D. A. Hollowell et al. Anal. Chem. 1986, 58, 1524–1527.
T. Aoki et al. Chem. Abstr. 1987, 107, 161193h.
T. Aoki et al. Chem. Abstr. 1988, 108, 156173t.
Y. Kanada et al. Anal. Chem. 1990, 62, 2084–2087.
J. L. P. Pavon et al. Anal. Chem. 1992, 64, 923–929.
H. Zhao et al. Am. J. Physiol, 1994, 267, C385–C393.
J. S. Beckman et al. Methods 1995, 7, 35–39.
A. J. Dunham et al. Anal. Chem. 1995, 67, 220–224.
G. E. Collins et al. "Field Screening Methods Hazard. Wastes Toxic Chem., Pro. Int. Symp." 1995, vol. 1, pp. 196–203.
X. Zhou et al. Anal. Chem 1996, 68, 1748–1754.
A. Aneman et al. Am. J. Physiol. 1996, 271, G1039–G1042.
Maria Cecilia Carreras et. al., "Kinetics of nitric oxide and hydrogen peroxide production and formation of peroxynitrite during the respiratory burst of human neutrophils," FEBS Letters 341 (1994) 65–68.
Kikuchi et. al., "Detection of Nitric Oxide Production from a Perfused Organ by a Luminol–H2O2 System," Anal. Chem. 1993, 65, 1794–1799.
Kikuchi et. al., "Real Time Measurement of Nitric Oxide Produced ex Vivo by Luminol–H2O2 Chemiluminescence Method," 268 J. Biol. Chem. 23106–23110 (1993).
Radi et. al., "Peroxynitrite–induced luminol chemiluminescence," 290 Biochem. J. 51–57 (1993).

(List continued on next page.)

*Primary Examiner*—Arlen Soderquist
*Attorney, Agent, or Firm*—Lyon & Lyon LLP

[57] ABSTRACT

A detector for detecting and measuring nitric oxide. Gas-permeable capillary membrane fibers transport a reagent solution through a plenum containing gases to be measured. Nitric oxide molecules penetrate the walls of the fibers and undergo a chemiluminescent reaction within. The fibers and the plenum are translucent, allowing photons emitted by the chemiluminescent reaction to escape and be detected by a photodetector. The reagent is buffered at an alkaline pH and mixed with the enzyme carbonic anhydrase to minimize the measurement errors caused by the presence of carbon dioxide in the gas to be measured.

13 Claims, 2 Drawing Sheets

OTHER PUBLICATIONS

Kelly et. al., "An Assessment of the Luminol Chemiluminescence Technique For Measurement of NO2 in Ambient Air," 24A Atmospheric Environment 2397–2403 (1990).

Schiff et. al., "Atmospheric Measurements of Nitrogen Dioxide with a Sensitive Luminol Instrument," 30 Water, Air and Soil Pollution 105–114 (1986).

Wendel et. al., "Luminol–Based Nitrogen Dioxide Detector," 55 Anal. Chem. 937–940 (1983).

Maeda et. al., "Chemiluminescence Method for the Determination of Nitrogen Dioxide," 52 Anal. Chem. 307–311 (1980).

NITRIC OXIDE DETECTOR

FIELD OF THE INVENTION

This invention generally relates to gas analysis, and more particularly to the detection and measurement of nitric oxide in gases such as air and human breath.

BACKGROUND OF THE INVENTION

At present, gaseous nitric oxide (NO) is most commonly measured by mixing a gas sample with ozone gas at low pressures. When a nitric oxide molecule reacts with an ozone ($O_3$) molecule, it forms nitrogen dioxide ($NO_2$) and oxygen ($O_2$) and emits a photon in the process. This photon possesses a red or near-infrared wavelength. The concentration of nitric oxide in the gas sample is thus determined by measuring the intensity of those photons. However, red and near-infrared wavelengths are not detected efficiently by standard photodetecting devices such as photomultiplier tubes and photodiodes. Consequently, special photodetector devices that are more sensitive to red light must be used. These devices must be cooled to subambient levels to reduce background noise from thermal effects. These special devices and their cooling requirements add cost and complexity over that required to measure visible light.

In addition, an ozone-based nitric oxide gas detector requires a vacuum pump and a method for making ozone, which is typically a high-voltage electrical discharge. As a result, ozone-based detectors are generally bulky and complex, and require a significant amount of electricity to operate. The high voltage required to operate an ozone-based detector can pose a safety risk to the user and to those nearby. OSHA regulations restrict allowable ozone exposure, making it difficult to use ozone-based nitric oxide gas detectors in the workplace. Furthermore, ozone is a toxic gas, and it must be vented or destroyed after use. Because ozone is a pollutant, environmental regulations may prohibit venting the ozone in many areas, forcing the user of an ozone-based detector to destroy the ozone after use. Destruction of the ozone adds an additional step, and additional cost, to the nitric oxide measurement process.

Gaseous nitric oxide may also be detected by placing a gas sample in contact with an alkaline luminol solution containing hydrogen peroxide. As with the ozone-based method of detection, the chemical reaction between nitric oxide and the luminol solution results in the emission of photons. Unlike the ozone-based method of detection, these photons possess wavelengths in the more energetic end of the visible light spectrum. While the luminol-based method of detection overcomes some of the problems of ozone-based detection, it possesses drawbacks of its own.

When measuring atmospheric nitric oxide, carbon dioxide levels are typically too low (300–400 parts per million (PPM), which is 0.03–0.04 percent) to interfere with the measurement. However, carbon dioxide typically constitutes several percent of exhaled human or animal breath. This amount of carbon dioxide is orders of magnitude greater than the amount present in the atmosphere. At present, this amount of carbon dioxide interferes with the detection and measurement of nitric oxide in human or animal breath. This interference primarily occurs in three ways. First, at a concentration of several percent, carbon dioxide reacts with the luminol solution to produce the same number of photons produced by the reaction of several parts per billion (PPB) of nitric oxide with luminol, tricking the detector into registering the presence of several PPB of nitric oxide which is not present in the sample. Second, carbon dioxide is known to react with a key intermediate in the nitric oxide/luminol reaction, ionic peroxynitrite ($ONOO^-$). This reaction reduces the response of the luminol solution to nitric oxide, causing the detector to measure less nitric oxide than is actually present. Third, some gaseous carbon dioxide will dissolve in the alkaline luminol solution, changing its pH and thereby reducing the standing background signal of the luminol solution.

SUMMARY OF THE INVENTION

The present invention is directed toward a nitric oxide gas detector for detecting the presence and measuring the concentration of nitric oxide in gases such as air and human breath.

In a first aspect of the invention, gas-permeable capillary membrane fibers transport a reagent solution through a larger plenum containing gases to be measured. The capillary membrane fibers are constructed of a material porous enough, and are thin enough, to allow nitric oxide molecules to penetrate through their walls and undergo a chemiluminescent reaction within. The capillary membrane fibers and plenum are translucent, allowing photons emitted by the chemiluminescent reaction to pass through and be detected by a photodetector.

In a second aspect of the invention, the reagent is buffered at an alkaline pH and mixed with the enzyme carbonic anhydrase to minimize the effect of carbon dioxide. The buffer reduces the pH effect of carbon dioxide, and the carbonic anhydrase reacts with carbon dioxide to form other chemical species in solution which do not interfere with the detection and measurement of nitric oxide.

In a first alternate embodiment of the invention, a gas-permeable membrane within a plenum separates a first space containing gases to be measured from a second space containing a reagent. The membrane is thin enough and porous enough to enable gaseous nitric oxide molecules to pass through and undergo a chemiluminescent reaction with the reagent in the second space. The plenum is translucent, allowing photons emitted by the chemiluminescent reaction to pass through and be detected by a photodetector.

In a second alternate embodiment of the invention, the portion of the reagent 18 that produces a chemiluminescent reaction with gaseous nitric oxide is not present in the reagent when the gaseous nitric oxide is exposed to the reagent. Preferably, luminol is used to produce a chemiluminescent reaction. Rather, the luminol is added in a second chamber, where the light produced by the chemiluminescent reaction is measured by a photodetector. Optionally, a carbonic anhydrase solution may be added in this second chamber to minimize the effect of carbon dioxide when nitric oxide is being measured in an environment containing a high concentration of carbon dioxide.

DETAILED DESCRIPTION OF THE PREFERRED EMBODIMENTS

Figure 1:
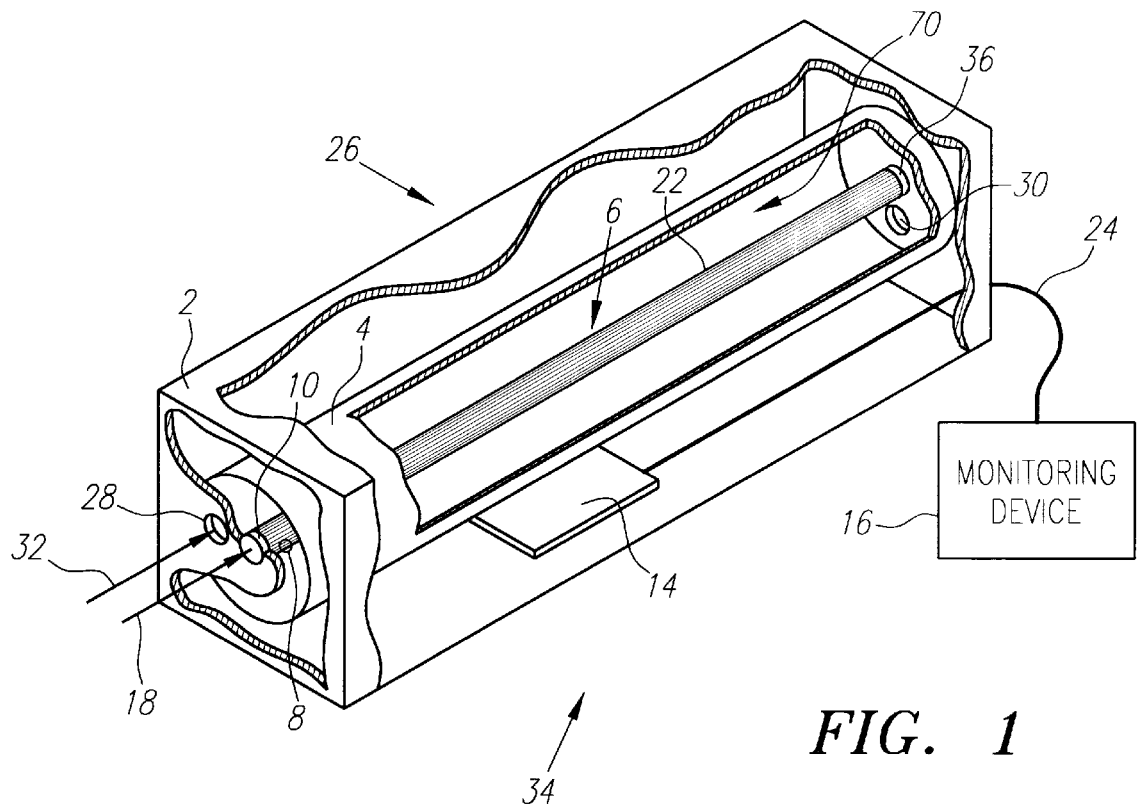
FIG. 1 is a schematic view of a nitric oxide gas detector utilizing capillary membrane fibers.

Referring to FIG. 1, an opaque enclosure 2 may be seen. The opaque enclosure 2 and its contents are referred to as the gas exchange module 26. A gas 32 in which the presence or concentration of nitric oxide is desired to be measured enters the gas exchange module 26 through an inlet port 28 in a wall of the opaque enclosure 2. The inlet port 28 leads to a chamber 70 that forms part of the interior of a plenum 4. To produce a flow of gas 32 into the inlet port 28, a vacuum pump or other suction device may be attached to an outlet port 30. Preferably, the outlet port 30 is located at the opposite end of the plenum 4 from the inlet port 28. However, the outlet port 30 may be placed at any location on the plenum 4 which allows the gas 32 to be sampled to enter the plenum 4 and substantially replace the ambient gas previously reposing in the plenum 4. Alternatively, the gas exchange module 26 may be placed in line or in parallel with a gas line or duct, such that the flow of gas through such gas line or duct impels gas 32 into the inlet port 28 and out of the outlet port 30. Alternatively, some applications of this device, such as atmospheric measurements or some types of medical applications, may not require the active production of gas flow into the gas exchange device 26, in which case gases to be sampled would enter the gas exchange device 26 through either the inlet port 28 or the outlet port 26 due to gas motion in the ambient environment.

After the gas 32 has entered the plenum 4 within the gas exchange module 26, the gas 32 comes into contact with one or more capillary membrane fibers 8. Preferably, one or more capillary membrane fibers 8 are organized into a fiber bundle 6. However, the capillary membrane fibers 8 may extend into the plenum 4 independently of one another. Preferably, the fiber bundle 6 is composed of approximately fifty capillary membrane fibers 8. These capillary membrane fibers 8 are preferably substantially parallel within the fiber bundle 6, but they may be twisted or wrapped together into a fiber bundle 6. Preferably, the capillary membrane fibers 8 extend through substantially the entire length of the plenum 4. Each capillary membrane fiber 8 is connected at one end to an inlet connector 10 and at the other end to an outlet connector 36. One side of the inlet connector 10 is connected to one end of each of the capillary membrane fibers 8 that compose the fiber bundle 6. Preferably, the connection between each capillary membrane fiber 8 and the inlet connector 10 is accomplished by epoxy adhesive. However, the connection may be accomplished by any means which do not substantially restrict flow of a reagent 18 from the inlet connector 10 into the capillary membrane fibers 8. The other side of the inlet connector 10 possesses at least one opening for the reagent 18 to enter, and provides for more convenient operation by an operator, who does not have to make individual small-scale connections to each capillary membrane fiber 8. The capillary membrane fibers 8 attach to the outlet connector 36 in the same manner, and the outlet connector 36 also possesses at least one opening for the reagent 18 to exit.

As shown in FIG. 1, the inlet connector 10 and the outlet connector 36 are attached to the walls of the opaque enclosure 2. Also as shown in FIG. 1, each end of the plenum 4 is attached to a wall of the opaque enclosure 2. However, any structural configuration may be used that supports the plenum 4 and the fiber bundle 6 within the opaque enclosure 2.

The reagent 18 flows into the gas exchange module 26 through the inlet connector 10, from there flowing into the capillary membrane fibers 8 composing the fiber bundle 6. The reagent 18 may be induced to flow into the gas exchange module 26 by gravity, by pumping, by suction, or by any other means which can induce a sufficient flow rate of the reagent 18.

Each capillary membrane fiber 8 possesses a wall 22. The wall 22 must be composed of a porous material sufficiently thin to allow gaseous nitric oxide molecules to pass through into the interior space within the capillary membrane fiber 8. However, the molecules of the reagent 18 are approximately the same size as the molecules of nitric oxide. Consequently, the wall 22 must also be composed of a material which is not permeable to molecules of the same size in liquid form, and which is hydrophobic enough to repel the water which comprises a fraction of the reagent 18. Polypropylene simultaneously possesses all these properties, and is the preferred material for the wall 22.

The wall 22 must also be thick enough to prevent rupture of the capillary membrane fibers 8 as the reagent 18 flows through. The pressure within each capillary membrane fiber 8 is a function of the flow rate of the reagent 18. The preferred flow rate of the reagent 18 is 0.5 to 5 milliliters per minute, and the wall 22 is preferably composed of polypropylene 50 microns thick.

Nitric oxide in the gas 32 is thus brought into contact with the reagent 18 within the capillary membrane fibers 8. The reagent 18 contains two components. First, the reagent 18 contains an alkaline solution of hydrogen peroxide and a chemiluminescent reactant. Luminol itself is preferably used as the chemiluminescent reactant in the reagent 18, but any analogous substance, such as isoluminol, AHEI, ABEI, ABEI-NCS, luciferan, cypridina luciferan, CLA, or MCLA may be used. This component of the reagent 18 is responsible for the chemiluminescent reaction that detects nitric oxide. A chemiluminescent reaction is a chemical reaction in which light is emitted. It is known that the reaction of nitric oxide with a luminol/hydrogen peroxide solution is chemiluminescent. Consequently, the presence and concentration of nitric oxide in the plenum 4 is ascertained by the amount of light detected from this chemiluminescent reaction.

The presence of carbon dioxide in the gas 32 causes error in the measurement of nitric oxide. Carbon dioxide will react with the reagent 18 in a chemiluminescent reaction, creating photons which are measured as the result of nitric oxide. Thus, carbon dioxide causes a false positive response for nitric oxide. This effect is small and relatively constant at atmospheric concentrations of carbon dioxide and nitric oxide, and typically can be ignored. However, the effect of carbon dioxide on the reagent 18 must be minimized when the concentration of carbon dioxide in the gas 32 rises to above approximately one percent. An example is the measurement of nitric oxide in human breath, which is approximately five percent carbon dioxide. To properly measure nitric oxide levels in a gas 32 with such a high level of carbon dioxide, its effect must be minimized.

The second component of the reagent 18 is a reactant which minimizes the effects of carbon dioxide. In the preferred embodiment, the effects of carbon dioxide are minimized by a chemical reaction with the enzyme carbonic anhydrase. However, those effects can also be minimized by other chemicals that react rapidly with carbon dioxide as compared to luminol, and by other methods such as measuring the effect of carbon dioxide alone and subtracting that effect from the combined measurement. Carbon dioxide may also be removed from the sample gas by physical means such as molecular sieves, chemical absorbers, or the addition of gas with a high carbon dioxide concentration to raise the level of the background signal above the carbon dioxide concentration of the sample.

In the preferred embodiment, carbonic anhydrase reacts rapidly with carbon dioxide that comes into contact with the reagent, forming carbonic acid ($H_2CO_3$), bicarbonate ($HCO_3^-$) ions, and carbonate ($CO_3^{--}$) ions in solution. By reacting with carbon dioxide molecules that enter the reagent 18, carbonic anhydrase minimizes the measurement error introduced by the presence of carbon dioxide in the gas 32. Preferably, the concentration of carbonic anhydrase used is 1 to 10 milligrams per liter.

The reagent 18 is alkaline. To further minimize the undesirable effects of carbon dioxide, the reagent 18 is buffered. The reagent 18 is partly composed of water. Water reacts with carbon dioxide to form carbonic acid. Consequently, carbon dioxide will render the reagent 18 more acidic. At a high concentration of carbon dioxide, such as that present in human breath, this acidification becomes significant enough to alter the chemiluminescent reaction in a manner that interferes with the detection of nitric oxide. Therefore, to accurately measure the concentration of nitric oxide in a gas mixture containing a high concentration of carbon dioxide, the reagent 18 must be buffered. Preferably, the reagent 18 is buffered with a mixture of carbonate and bicarbonate at a 0.05 to 0.5 molar concentration.

The capillary membrane fibers 8 are translucent, enabling the photons produced by the chemiluminescent reaction between nitric oxide and the reagent 18 to escape. A translucent material is one which transmits light. Consequently, a transparent material, which transmits light without appreciable scattering, is here defined as a subset of the set of translucent materials. As stated above, the capillary membrane fibers 8 are preferably composed of polypropylene. Similarly, the plenum 4 is translucent. Preferably, the plenum 4 is composed of a translucent polymer. However, silica or other translucent or transparent materials may be used. A photodetector 14 is located within the opaque enclosure 2. The opaque enclosure 2 prevents outside light from striking the photodetector 14. Preferably, the photodetector 14 is mounted to an interior wall of the opaque enclosure 2. However, the photodetector 14 may be mounted to the plenum 4 or to any other structure within the opaque enclosure 2 where the photodetector 14 can view photon emission from the fiber bundle 6. Preferably, the photodetector 14 is a photomultiplier tube. However, the photodetector may be a photodiode or other device for detecting photons and reporting photon detection in digital or analog form. The photodetector 14 measures the intensity of light emitted from the fiber bundle 6 as a result of the chemiluminescent reaction between nitric oxide and the reagent 18.

The luminol/hydrogen peroxide solution will react with trace amounts of metal ions in a chemiluminescent reaction. Consequently, a small number of photons are produced in the fiber bundle 6 as a result of unavoidable metal contamination of the reagent 18, creating an elevated background signal. Fluctuations in that background contribute to noise in the measurement. However, the amount of background noise is small enough to allow measurement of nitric oxide to a concentration of one part per billion or less.

The photodetector 14 transmits information regarding the intensity of light detected to a monitoring device 16. Preferably, a cable 24 is used to transmit this information. However, the photodetector may transmit information regarding light intensity to a monitoring device 16 by wireless transmission without diminishing the functionality of the invention. Preferably, the monitoring device 16 is a computer capable of recording and displaying the light intensity information it receives from the photodetector 14. However, any device capable of recording, displaying, or manipulating the information received from the photodetector 14 may be used. The nitric oxide gas detector 34 is calibrated at the factory or by the user, such that a given intensity of light measured by the photodetector 14 corresponds to a specific concentration of nitric oxide in the gases sampled within the plenum 4. Consequently, the measuring device 16 can convert light intensity measurements from the photodetector 14 to nitric oxide concentration levels in the sampled gas 32. Alternatively, the measuring device 16 can store the light intensity information transmitted from the photodetector 14 for later conversion to nitric oxide concentration data. The photodetector 14 is enclosed within the opaque enclosure 2. Preferably, the photodetector 14 is located in close proximity to the plenum 4. However, the photodetector 14 may be placed in contact with the plenum 4 if such contact will not interfere with the operation of the photodetector 14. Further, the photodetector 14 may be placed further from the tube 14, as long as light from the chemiluminescent reactions in the fiber bundle 6 can reach it.

In an alternate embodiment, the monitoring device 16 may be included in the photodetector 14 or attached to the photodetector 14 within the opaque enclosure 2. Such a monitoring device may be an application-specific integrated circuit (ASIC), a microprocessor, or another device for converting light intensity measurements to nitric oxide concentration data.

In an alternate embodiment, gas 32 flows through the capillary membrane fibers 8 and the reagent 18 flows through the plenum 4. In this embodiment the walls of the capillary membrane fibers need not transmit light, as the chemiluminescent reaction between the reagent 18 and the nitric oxide molecules takes place in the plenum 4, rather than in the capillary membrane fibers 8.

Figure 2:
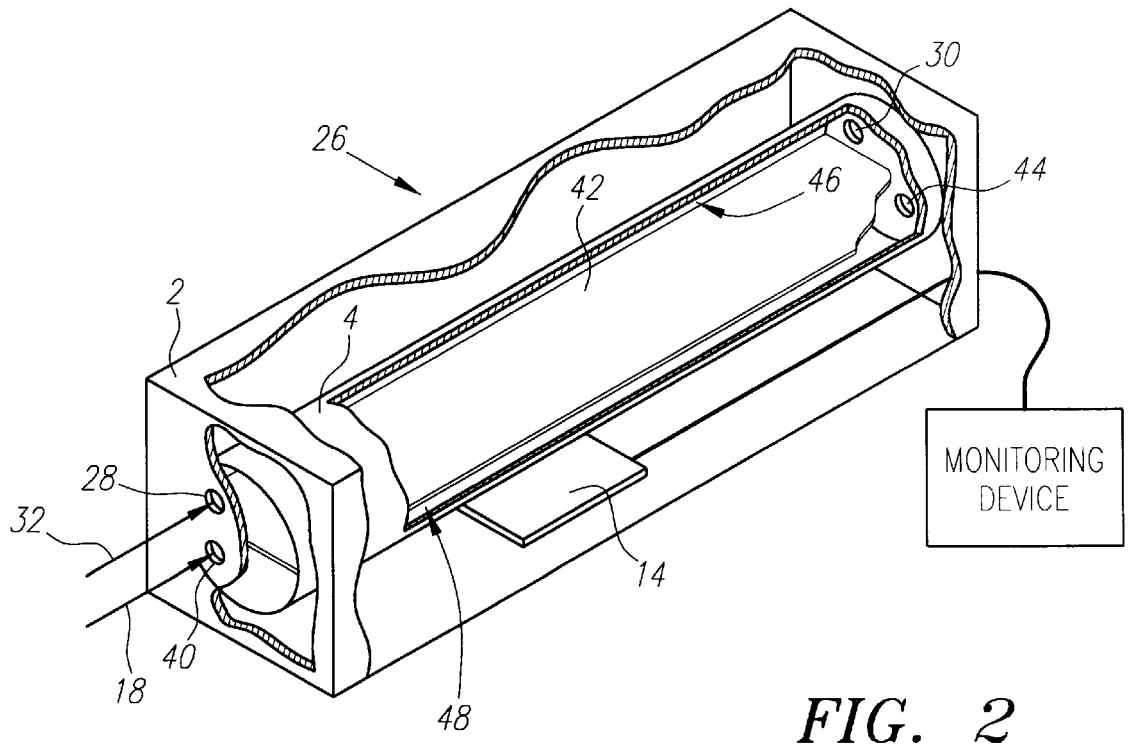
FIG. 2 is a schematic view of a nitric oxide gas detector utilizing a membrane.

In an alternate embodiment of the gas exchange module 26, a membrane is used for gas exchange instead of translucent capillary membrane fibers. Referring now to FIG. 2, a membrane 42 divides the interior of the plenum 4 into two separate spaces, a first space 46 and a second space 48. The first space 46 and the second space 48 need not enclose equal volumes. Gas 32 enters the first space 46 within the plenum 4 in the gas exchange module 26 through the inlet port 28. The reagent 18 enters the second space 48 in the plenum 4 through a second inlet port 40.

Nitric oxide from the gas 32 within the first space 46 passes through the membrane 42 into the reagent 18 in the second space 48. The criteria for selecting a material and a thickness for the membrane 42 are the same as apply to the wall 22 in the first embodiment above. The chemiluminescent reaction between nitric oxide and the reagent 18 occurs within the second space 48.

The membrane 42 need not be translucent. However, the plenum 4 must be translucent in order for light to escape and be sensed by the photodetector 14. The photodetector 14 must be located within the gas exchange module 26 such that light from the chemiluminescent reactions in the second space 48 can reach it. Preferably, the photodetector 14 is attached to the opaque enclosure 2 in close proximity to the plenum 4 on the same side as the second space 48, particularly if the membrane 42 is opaque.

In an alternate embodiment of the nitric oxide gas detector 2, the chemiluminescent reaction between nitric oxide and the reagent 18 does not occur within the gas exchange module 26. The gas exchange module 26 operates as disclosed above, with the exception that the reagent 18 does not contain luminol or carbonic anhydrase. Rather, the reagent 18 is simply composed of water and a buffered alkaline peroxide solution. Because luminol is not present in the reagent 18, the chemiluminescent reaction does not take place in the gas exchange module 26. Consequently, neither the plenum 4 nor the capillary membrane fibers 8 need be translucent. Alternately, if the membrane 42 is used for gas exchange, it need not be translucent. Further, the enclosure 2 need not be opaque. Nitric oxide within the gas sampled in the gas exchange module diffuses into the buffered alkaline peroxide solution. Finally, the photodetector 14 is not present within the gas exchange module 26.

Figure 3:
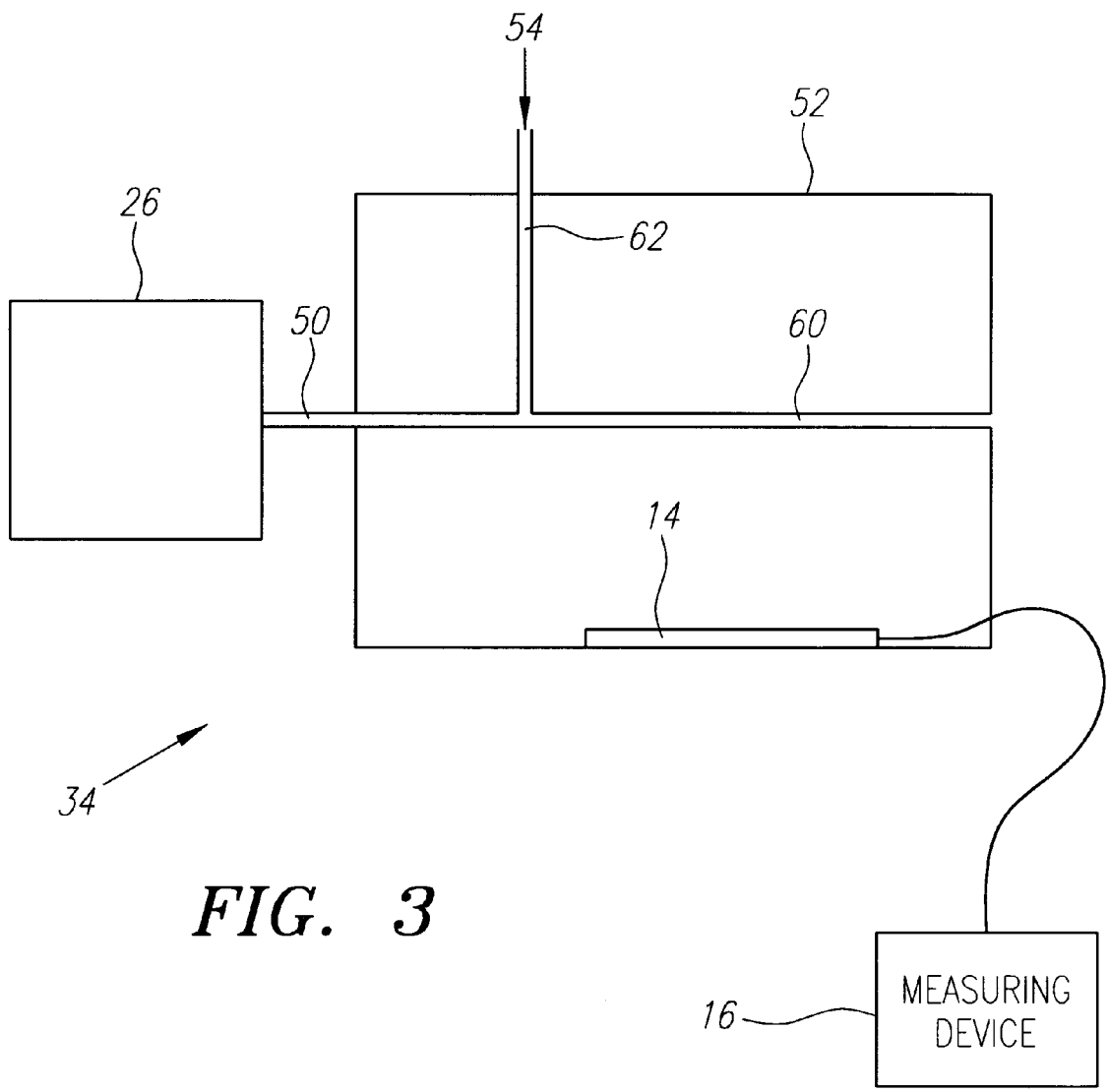
FIG. 3 is a schematic view of a nitric oxide gas detector in which the gas exchange module is separated from the housing in which chemiluminescence occurs.

Referring now to FIG. 3, a tube 50 exits the gas exchange module. A buffered alkaline peroxide solution travels through the tube 50, carrying nitric oxide and its reaction products in solution from the gas exchange module 26. The tube 50 enters an opaque housing 52. Within the opaque housing 50, luminol 54 is introduced through a second tube 62 into the buffered alkaline peroxide solution within tube 50. The chemiluminescent reaction between the luminol 54 and the nitric oxide in the buffered alkaline peroxide solution then begins. Consequently, a segment 60 of the tube 50 downstream of the intersection of the tube 50 and the second tube 62 must be translucent. Light from the chemiluminescent reaction travels through the segment 60, striking the photodetector 14. The photodetector 14 then transmits data to the measuring device 16, as disclosed above for the primary embodiment of the nitric oxide gas detector 34. The tube 50 cannot be permeable to nitric oxide gas or to the reagent within. Introduction of nitric oxide gas into tube 50 after the gas exchange module 26 would create a measurement error.

Optionally, a solution of carbonic anhydrase may be introduced into the tube 50. This is preferably accomplished through the second tube 62 along with the introduction of luminol into the tube 50. However, carbonic anhydrase may be introduced separately into the tube 50 at any location upstream from the intersection of the second tube 62 with the tube 50. Addition of carbonic anhydrase is desirable when nitric oxide concentration is to be measured in an environment containing a high level of carbon dioxide. The carbonic anhydrase 56 need not be introduced into the tube 50 when nitric oxide is to be measured in an environment containing a low level of carbon dioxide.

A preferred nitric oxide gas detector and many of its attendant advantages have thus been disclosed. It will be apparent, however, that various changes may be made in the form, construction, and arrangement of the parts without departing from the spirit and scope of the invention, the form hereinbefore described being merely a preferred or exemplary embodiment thereof. Therefore, the invention is not to be restricted or limited except in accordance with the following claims.

What is claimed is:

1. A nitric oxide gas detector, comprising:
   a translucent plenum with fluid connectors attached thereto;
   an inlet port providing entry into a chamber in the translucent plenum through which a gas to be analyzed enters;
   an outlet port providing an exit from the translucent plenum through which the gas exits;
   a reagent which participates in a chemiluminescent reaction with nitric oxide, the reagent containing carbonic anhydrase in a concentration of 1 to 10 milligrams per liter;
   a plurality of translucent capillary membrane fibers within the translucent plenum, the fiber or fibers attached to the fluid connectors, the reagent flowing within the fiber or fibers, the fiber or fibers allowing gaseous nitric oxide molecules to diffuse thereinto and preventing the reagent from substantially diffusing into the chamber in the translucent plenum;
   an opaque enclosure, inside which the translucent plenum is located;
   a photodetector which measures light produced by the chemiluminescent reaction between the reagent and nitric oxide; and
   a monitoring device which is adapted to receive data from the photodetector.

2. A nitric oxide gas detector, comprising:
   a translucent plenum;
   an inlet port in the translucent plenum through which a gas in which nitric oxide is to be detected enters;
   an outlet port in the translucent plenum through which gas exits;
   a reagent which participates in a chemiluminescent reaction with nitric oxide, the reagent containing an alkaline solution of luminol and hydrogen peroxide, the reagent containing carbonic anhydrase in a concentration of 1 to 10 milligrams per liter, and the reagent being buffered with a mixture of carbonate and bicarbonate in a 0.05 to 0.5 molar concentration;
   one or more translucent capillary membrane fibers within the translucent plenum, the reagent flowing within the translucent capillary membrane fiber or fibers, the translucent capillary membrane fiber or fibers being composed of material sufficiently thin and porous to allow gaseous nitric oxide molecules to diffuse into the translucent capillary membrane fiber or fibers and sufficiently hydrophobic to prevent the reagent from substantially diffusing out of the translucent capillary membrane fiber or fibers;
   an opaque enclosure, inside which the plenum is located;
   a photodetector which measures light produced by the chemiluminescent reaction between the reagent and nitric oxide; and
   a monitoring device which processes data from the photodetector.

3. A nitric oxide gas detector, comprising:
   a plenum composed of translucent polymer with fluid connectors attached thereto;
   an inlet port in the plenum through which a gas to be analyzed enters;
   an outlet port in the plenum through which the gas exits;
   a reagent which participates in a chemiluminescent reaction with nitric oxide, the reagent containing an alkaline solution of luminol and hydrogen peroxide, the reagent containing carbonic anhydrase in a concentration of 1 to 10 milligrams per liter, and the reagent being buffered with a mixture of carbonate and bicarbonate in a 0.05 to 0.5 molar concentration;
   a plurality of translucent capillary membrane fibers within the translucent plenum which attach to the fluid connectors, the reagent flowing within the translucent capillary membrane fibers, the translucent capillary membrane fibers being composed of polypropylene and having a wall thickness of 50±20 microns,
   an opaque enclosure, inside which the plenum is located;
   a photodetector which measures light produced by the chemiluminescent reaction between the reagent and nitric oxide; and
   a monitoring device which records, displays or otherwise manipulates data from the photodetector.

4. A nitric oxide gas detector, comprising:

a reagent which participates in a chemiluminescent reaction with nitric oxide, the reagent containing an alkaline solution of luminol and hydrogen peroxide and containing carbonic anhydrase in a concentration of 1 to 10 milligrams per liter, the reagent being buffered with a mixture of carbonate and bicarbonate in a 0.05 to 0.5 molar concentration;

a translucent plenum;

a membrane dividing the translucent plenum into a first space and a second space, the membrane being composed of material sufficiently thin and porous to allow gaseous nitric oxide molecules in the first space to diffuse through the membrane into the second space, and sufficiently hydrophobic to prevent the reagent in the second space from substantially diffusing through the membrane into the first space;

an inlet port in the translucent plenum through which a gas to be analyzed enters the first space;

an outlet port in the translucent plenum through which the gas exits the first space;

an inlet port in the translucent plenum through which the reagent enters the second space;

an outlet port in the translucent plenum through which the reagent exits the second space;

an opaque enclosure, inside which the plenum is located;

a photodetector which measures light produced by the chemiluminescent reaction between the reagent and nitric oxide; and a monitoring device which is adapted to receive data from the photodetector.

5. A nitric oxide gas detector, comprising:

a gas exchange module;

a reagent containing buffered alkaline peroxide;

a first tube attached to the gas exchange module through which the reagent exits the gas exchange module;

an opaque housing connected to the first tube;

a second tube connecting to the first tube and introducing into the reagent within the first tube a solution which participates in a chemiluminescent reaction with nitric oxide, the second tube also introducing carbonic anhydrase into the reagent in the first tube;

a third tube connecting to the first tube downstream of the connection between the first tube and the second tube, the third tube being translucent;

a photodetector which measures light produced by the chemiluminescent reaction between the reagent and nitric oxide; and a monitoring device which is adapted to receive data from the photodetector.

6. A detector for determining the concentration of nitric oxide in a gas, comprising:

reagent containing buffered alkaline peroxide;

a plenum having a fluid inlet connector and a fluid outlet connector;

an inlet port on the plenum through which a gas to be analyzed enters;

an outlet port in the plenum through which the gas exits;

a plurality of capillary membrane fibers within the plenum, each of which attach on one end to the fluid inlet connector and on the opposite end to the fluid outlet connector, the reagent flowing within the fibers, the fibers being composed of material sufficiently thin and porous to allow gaseous nitric oxide molecules to diffuse into the fibers and sufficiently hydrophobic to prevent the reagent from substantially diffusing out of the fibers;

an opaque housing;

a first tube attached to the fluid outlet connector and extending into the opaque housing, at least a portion of the first tube located within the opaque housing being translucent;

a second tube connecting to the first tube and introducing into the reagent within the first tube a solution which participates in a chemiluminescent reaction with nitric oxide, wherein carbonic anhydrase is introduced into the reagent separately from and upstream from the solution which participates in a chemiluminescent reaction with nitric oxide; and a photodetector which measures light produced by the chemiluminescent reaction between the reagent and nitric oxide.

7. A method for measuring the concentration of gaseous nitric oxide in a gas sample, comprising the steps of:

inducing a flow of a reagent containing an alkaline solution of luminol and hydrogen peroxide through one or more translucent capillary membrane fibers composed of material sufficiently thin and porous to allow gaseous nitric oxide molecules within the gas sample to diffuse into the translucent capillary membrane fiber or fibers and sufficiently hydrophobic to prevent the reagent from substantially diffusing out of the translucent capillary membrane fiber or fibers;

buffering the reagent with a mixture of carbonate and bicarbonate at a 0.05 to 0.5 molar concentration;

adding carbonic anhydrase to the reagent at a concentration of 1 to 10 milligrams per liter;

passing the gas sample over the surface of the translucent capillary membrane fiber or fibers; and measuring the amount of light generated by the chemiluminescent reaction between the reagent and the gas which has passed through the walls of the translucent capillary membrane fiber or fibers.

8. A method for measuring the concentration of nitric oxide in a gas, comprising the steps of:

inducing a flow of a reagent containing a buffered alkaline peroxide solution through one or more translucent capillary membrane fibers composed of material sufficiently thin and porous to allow gaseous nitric oxide molecules to diffuse into the translucent capillary membrane fiber or fibers and sufficiently hydrophobic to prevent the reagent from substantially diffusing out of the translucent capillary membrane fiber or fibers;

passing the gas over the surface of the translucent capillary membrane fiber or fibers;

conducting the reagent into an opaque enclosure;

adding a solution which participates in a chemiluminescent reaction with nitric oxide to the reagent;

adding a carbonic anhydrase solution to the reagent if the gas to be analyzed contains a high percentage of carbon dioxide; and measuring the amount of light generated by the chemiluminescent reaction.

9. The method of claim 8, wherein the solution contains luminol.

10. A method for measuring the concentration of nitric oxide in a gas, comprising the steps of:

inducing a flow of a reagent containing a buffered alkaline peroxide solution into and out of a first space, the first space bounded on at least one side by a porous membrane;

inducing a flow of the gas into and out of a second space, the second space bounded on at least one side by the porous membrane, the membrane sufficiently thin and permeable to allow gaseous nitric oxide molecules to diffuse through the membrane from the second space into the first space, and sufficiently hydrophobic to prevent the reagent from substantially flowing through the membrane from the first space into the second space;

passing a gas to be sampled over the membrane;

conducting the reagent into an opaque enclosure;

adding a solution which participates in a chemiluminescent reaction with nitric oxide to the reagent;

adding a carbonic anhydrase solution to the reagent if the gas to be analyzed contains a high percentage of carbon dioxide; and measuring the amount of light generated by the chemiluminescent reaction.

11. The method of claim 10, wherein the solution contains luminol.

12. A detector for determining the concentration of nitric oxide in a gas, comprising:

a reagent containing buffered alkaline peroxide;

a plenum having a fluid inlet connector and a fluid outlet connector, whereby the reagent enters the plenum through the fluid inlet connector and exits the plenum through the fluid outlet connector;

a membrane dividing the plenum into a first space and a second space, the membrane lying substantially in a single plane and being composed of material sufficiently thin and porous to allow gaseous nitric oxide molecules in the first space to diffuse through the membrane into the second space, and sufficiently hydrophobic to prevent the reagent in the second space from substantially diffusing through the membrane into the first space;

an inlet port in the plenum through which a gas to be analyzed enters the first space;

an outlet port in the plenum through which the gas exits the first space;

an opaque housing;

a first tube attached to the fluid outlet connector and extending into the opaque housing, at least a portion of the first tube located within the opaque housing being translucent;

a second tube connecting to the first tube and introducing into the reagent within the first tube a solution which participates in a chemiluminescent reaction with nitric oxide, wherein carbonic anhydrase is introduced through the second tube into the reagent in the first tube;

a photodetector which measures light produced by the chemiluminescent reaction between the reagent and nitric oxide; and a monitoring device adapted to receive data from the photodetector.

13. A detector for determining the concentration of nitric oxide in a gas, comprising:

a reagent containing buffered alkaline peroxide;

a plenum having a fluid inlet connector and a fluid outlet connector, whereby the reagent enters the plenum through the fluid inlet connector and exits the plenum through the fluid outlet connector;

a membrane dividing the plenum into a first space and a second space, the membrane lying substantially in a single plane and being composed of material sufficiently thin and porous to allow gaseous nitric oxide molecules in the first space to diffuse through the membrane into the second space, and sufficiently hydrophobic to prevent the reagent in the second space from substantially diffusing through the membrane into the first space;

an inlet port in the plenum through which a gas to be analyzed enters the first space;

an outlet port in the plenum through which the gas exits the first space;

an opaque housing;

a first tube attached to the fluid outlet connector and extending into the opaque housing, at least a portion of the first tube located within the opaque housing being translucent;

a second tube connecting to the first tube and introducing into the reagent within the first tube a solution which participates in a chemiluminescent reaction with nitric oxide, wherein carbonic anhydrase is introduced into the reagent separately from and upstream from the solution which participates in a chemiluminescent reaction with nitric oxide;

a photodetector which measures light produced by the chemiluminescent reaction between the reagent and nitric oxide; and a monitoring device adapted to receive data from the photodetector.

* * * * *